United States Patent [19]

Pradhan et al.

[11] Patent Number: 4,994,393
[45] Date of Patent: Feb. 19, 1991

[54] BLOOD PARTITIONING COMPOSITION

[75] Inventors: Shrikant P. Pradhan, Parsippany, N.J.; Sheshadri Narayanan, New York, N.Y.; Fu-chung Lin, Wayne, N.J.

[73] Assignee: Becton, Dickinson and Company, Franklin Lakes, N.J.

[21] Appl. No.: 314,540

[22] Filed: Feb. 22, 1989

[51] Int. Cl.$^5$ .................. G01N 1/18; G01N 33/49
[52] U.S. Cl. .................................. 436/8; 436/174; 435/2; 210/516; 210/789; 252/60
[58] Field of Search .............. 436/8, 16, 17, 174; 252/60, 61; 435/2; 210/516, 789

[56] References Cited

U.S. PATENT DOCUMENTS

| | | | |
|---|---|---|---|
| 3,780,935 | 12/1973 | Lukacs et al. | 233/1 A |
| 3,852,194 | 12/1974 | Zine | 210/83 |
| 4,083,784 | 4/1978 | Zine, Jr. | 210/83 |
| 4,101,422 | 7/1978 | Lamont et al. | 210/84 |
| 4,148,764 | 4/1979 | Lamont et al. | 260/22 |
| 4,172,803 | 10/1979 | Ichikawa et al. | 252/60 |
| 4,230,584 | 10/1980 | Ichikawa et al. | 210/516 |
| 4,310,430 | 1/1982 | Ichikawa et al. | 252/60 |
| 4,350,593 | 9/1982 | Kessler | 210/516 |
| 4,457,782 | 7/1984 | Honda | 106/266 |
| 4,534,798 | 8/1985 | Honda | 106/266 |

FOREIGN PATENT DOCUMENTS 0044056  4/1981  Japan .................. 210/789

Primary Examiner—Robert A. Wax
Assistant Examiner—Janelle D. Waack
Attorney, Agent, or Firm—Robert P. Grindle

[57] ABSTRACT

A composition is provided for use, particularly in evacuated blood collection tubes, as a blood partitioning composition. The composition is useful in provididng cleaner serum or plasma samples for biochemical tests, including a wide range of drugs. The composition includes a balanced dual resin component which provides the desired hydrophobic property while simultaneously controlling viscosity and the specific gravity, which component is comprised of poly-alpha-pinene resin which provides good drug recovery but low density with a chlorinated hydrocarbon resin which provides the proper density level while maintaining the desired hydrophobic property of the resin blend. Thixotropic property is achieved by adding silica and network stabilizer in the composition.

8 Claims, 1 Drawing Sheet

BLOOD PARTITIONING COMPOSITION

BACKGROUND AND STATEMENT OF THE INVENTION

This invention relates to a liquid separating composition used for separating the components of a liquid substance under centrifugal force. More particularly, this invention relates to the separation of the relatively light normally liquid blood phase from a blood composition containing serum or plasma from a relatively heavy normally solid blood phase containing, for example, erythrocytes, platelets, etc., by subjecting the blood sample to centrifugation.

Biochemical tests carried out in a clinical laboratory require use of blood serum or plasma as a sample. For preparing the sample for examination, it is necessary to separate the blood serum or plasma from the solid blood components. Prior art methods for obtaining such separation include adding to a sample of blood a substance, or an object, or a combination of the two, having a specific gravity intermediate between serum or plasma and the solid blood component. Under centrifugal forces, this substance moves intermediate between the two types of blood components thereby forming a partitioning wall between them.

Representative wall-forming separation materials include those disclosed in U.S. Pat. Nos. 3,780,935 and 3,852,194, for example. These compositions are referred to as gel compositions or thixotropic compositions. Other patents which are directed to separation and/or barrier materials include, for example, U.S. Pat. No. 4,230,584, issued Oct. 28, 1980; U.S. Pat. No. 4,148,764 issued Apr. 10, 1979; U.S. Pat. No. 4,534,798, issued Aug. 13, 1985; U.S. Pat. No. 4,457,782, issued July 3, 1984; U.S. Pat. No. 4,172,803, issued Oct. 30, 1979; U.S. Pat. No. 4,101,422, issued July 18, 1978 and U.S. Pat. No. 4,310,430, issued Jan. 12, 1982. The '422 patent is directed to a polyester material useful in separation compositions, while the '584 patent is directed to a device for using the composition of the '803 patent. The remaining patents are directed to separation compositions of specific components for achieving specific separation results. None of them, however, are directed to a specific dual resin component as found in this invention which provides good stability of blood analytes and a wide range of groups of drugs.

The invention here, as discussed above, discloses a new thixotropic composition which may, for example, be useful for the improved recovery of imipramine. In the ideal separation of the type employing a thixotropic gel as the phase separation barrier component, the gel is characterized as compositionally stable, and physically stable in the absence of any substantial application of centrifugal force. Moreover, it is appropriate for the gel to form a strong cohesive barrier between the components desired to be separated, that the gel be chemically inert, and have a density which is intermediate that of the blood phases to be separated.

Compositionally stable compositions mean that the components are ingredients of the separating gel which will not separate under normal storage and/or use. The composition is basically an oil or an oil-like composition compounded with an inert filler. However, the composition should be stable enough that the oil or oil like material does not bleed or separate from the inert filler dispersed therein. Physically stable barrier materials will not move or change shape except when subjected to the application of centrifugal force. By chemically inert, it is meant that the barrier material should not be chemically reactive with the blood sample being separated, its constituents or reagents commonly employed in carrying out diagnostic testing of blood serum.

This invention constitutes an improvement over the prior art thixotropic gel compositions in that it has been discovered that a specific hydrocarbon resin such as poly-alpha-pinene has hydrophobic properties and gives superior recoveries for drugs with higher PKa values. However, this hydrocarbon resin has a lower density of about 0.99 which restricts the use of this material alone as being a possible candidate for a barrier gel. The Applicants here have discovered, quite unexpectedly, that by mixing a chlorinated hydrocarbon with this hydrocarbon to form a dual resin component, the density is increased to a level to formulate a thixotropic gel appropriate for centrifugal separation. Moreover, with this hydrocarbon and chlorinated hydrocarbon blend, adjustments can be made of the density of the final resin component as required for specific applications.

In considering generally the properties of the gel composition of the invention here, the composition contains a mixture of resin blends, as discussed above, with an adjusted specific gravity, preferably, ranging from within the range of between about 1.00 and 1.04 at 25° C., a radiation stabilizer, a short chain polyfunctional material as a network stabilizer and a thixotropic agent. The composition of the invention has a specific gravity at 25° C. generally within the range of between about 1.03 and 1.07, and a viscosity at 25° C. of within the range of between about 800,000 and 1,800,000 centipoises at a shearing rate of 1 second$^{-1}$.

The new gel composition is based upon hydrocarbon raw materials selected because they are more hydrophobic, in combination. Moreover, the new gel composition has a lower specific gravity and a higher viscosity. The new gel composition forms a complete and solid barrier with minimum red cell entrapment at 1,000 G force centrifugation. It provides the stability of blood analytes. Moreover, it provides good drug recovery and stability of a wide range of drugs.

In considering generally the composition for the invention here, a typical composition includes a resin blend, as discussed above, of a polyterpine resin and a chlorinated alpha olefin. The composition includes a radiation stabilizer such as Gamma Shield 401 or 801, products of M. & T. Chemicals Inc., Rahway, N. J., or epoxidized soybean oil, a network stabilizer such as glycerine, ethylene diamine, propylene glycol, or ethylene glycol, a thixotropic agent such as silica and a pigment such as titanium dioxide.

A preferred composition, in accordance with this invention, includes admixing within the range of between about 67 and 86 percent by weight polyterpine, within the range of between about 13 and 24 percent by weight chlorinated hydrocarbon, within the range of between about 2 and 6 percent by weight silica, within the range of between about 0.15 and 0.8 percent a short chain polyfunctional stabilizer, within the range of between about 0.015 and 0.03 percent titanium dioxide, and within the range of between about 2.3 and 15 percent epoxidized soybean oil. The chlorinated hydrocarbon used in the composition is selected to have a minimum of 50 percent chlorine. A specific source of the polyterpine resin (poly-alpha-pinene) is a product of Arizona Chemical Company designated Zonarex Alpha 25. A specific source of chlorinated hydrocarbon is DO8618 which is chlorinated octadecene, a product of Dover Chemical Corporation.

DETAILED DESCRIPTION OF THE DRAWING

Figure 1:
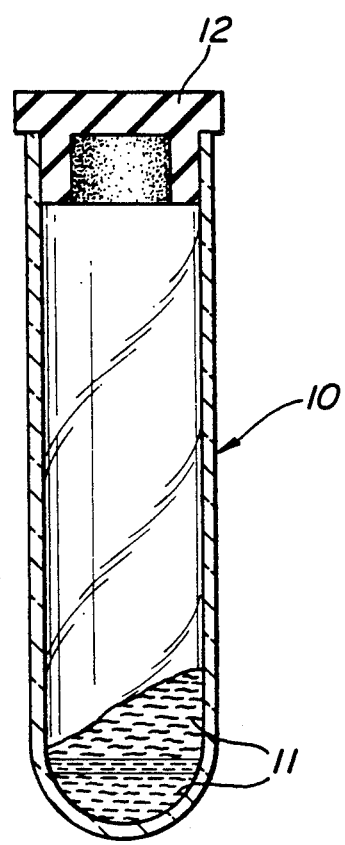

The single Figure shows a vertical sectional view of an evacuated container, illustrating the use of the gel composition of the invention.

As shown in the drawing, there is provided an evacuated tube 10, closed by a stopper 12, which has a gel composition 11, in accordance with the invention. A blood sample of interest can be transferred to tube 10, as known in the art, by piercing stopper 12 with a cannula. Subsequently, tube 10 is placed in a centrifuge in the usual manner and subjected to centrifugal force, as discussed in more detail below. This causes the composition 11 to become thixotropic and to move to a point dividing the heavier and lighter fractions of the sample introduced. For a further detailed review of this general procedure, reference is made to U.S. Pat. No. 4,350,593, issued Sept. 21, 1982.

As illustrative of a range of materials useful in the gel composition of the invention, one may note the following ranges:

| COMPONENT | WIDE RANGE WEIGHT PERCENT | PREFERRED RANGE WEIGHT PERCENT |
|---|---|---|
| A Poly-Alpha-Pinene | 67-86% | 70-77% |
| B Chlorinated Octadecene | 13-24% | 12.5-14.5% |
| C Epoxidized Soybean Oil | 2.3-15% | 4.5-7% |
| D Short Chain Polyfunctional Stabilizer | 0.1-0.8% | 0.4-0.6% |
| E Fumed Silica | 2-6% | 4.0-5.5% |
| F Titanium Dioxide | 0.015-0.03% | 0.02-0.03% |

As purely illustrative of the enhanced results achieved, in accordance herewith, one may note the following example in which a formulation, in accordance herewith is prepared as a thixotropic gel barrier medium for an evacuated blood collection tube. The composition was prepared and inserted into glass tubes which were subsequently stoppered and evacuated. Blood samples were introduced into the prepared tubes and placed under centrifugal force. Other tubes available on the market were used as the control for comparison purposes.

EXAMPLE

The following materials were admixed in percent by weight to form a representative composition according to the invention:

| A. Poly-Alpha-Pinene | 75.66% |
|---|---|
| B. Chlorinated Octadecene | 13.24% |
| C. Epoxidized Soybean Oil | 5.67% |
| D. Short Chain Polyfunctional Stabilizer | 0.40% |
| E. Fumed Silica | 5.00% |
| F. Titanium Dioxide | 0.03% |

The procedure for forming the composition included dispensing materials "A", "B" and "C" into a mix container, and adding "D." Thereafter, the admixture was heated and maintained at 60° C. Then, the admixture was blended under vacuum conditions. Following the blending, E and F were added and again blended under vacuum.

The gel material thus formed was dispensed into 20 conventional glass tubes used for blood sample separation procedures. In this connection, 1 to 2 gm. of the formed gel was dispensed into each tube, and then each tube was evacuated and stoppered in the usual manner, and sterilized by exposure to 1.5 MR of gamma irradiation.

At this point, representative blood samples were introduced into the tubes. After a dwell time of thirty minutes to simulate actual conditions, the tubes were subjected to centrifugation at 1000 G force. The gel in the tubes formed a barrier between blood cells and serum. Tubes were inverted and the gel barrier did not allow migration of cells into serum. After centrifugation, each of the tubes was examined closely and every tube indicated that the gel of the invention formed a clean barrier between the blood cell component of the introduced sample and the serum component. There was no indication of blood cells having migrated into the serum.

In order to establish drug recovery, another batch of 20 tubes were prepared as described above, and a control set of 20 non gel tubes were used, designated as Red Top VACUTAINER[R] Brand Tubes (Becton Dickinson VACUTAINER Systems, Rutherford, N. J.). The tubes were spiked with radiolabeled drugs including carbon 14 imipramine, carbon 14 lidocaine, carbon 14 of phenobarbitol, carbon 14 quinidine and tritium desmethylimipramine, after the introduction of the blood samples. The contents of the tubes were mixed gently. There, the tubes were subjected to centrifugation at 1000 G force. The radioactivity of the drugs present was read by a liquid scintillation counter and the percent of recovery was compared between the control tubes and the tubes containing the composition of the invention.

It was found that after the barrier formation the percent of recovery for the tubes containing the composition of the invention was 95-99 percent for the drugs tested (average of 20 tubes) as compared to the control.

Accordingly, as will be apparent from the foregoing, there is provided in accordance herewith methods and compositions for providing a new thixotropic gel composition for separating blood components which gel composition is based upon a hydrocarbon raw material and is more hydrophobic. The composition includes a resin component which achieves superior stability of blood analytes balanced with a chlorinated hydrocarbon which provides the appropriate control density level for the composition under centrifugal force. Furthermore, because of the chemical nature of the resin blend in the gel composition and lower density and higher viscosity of the gel, a more complete and solid barrier is achieved with the minimum of red cell entrapment at the specified centrifugal force.

While the methods and compositions herein disclosed form preferred embodiments of this invention, this invention is not limited to these specific methods and compositions, and changes can be made therein without departing from the scope of the invention which is defined in the appended claims.

What is claimed is:

1. A blood partitioning composition characterized by an admixture forming a thixotropic gel, said gel comprising (a) a dual resin component including poly-alpha-pinene of lower density combined with chlorinated octadecene of higher density;
(b) a radiation stabilizer;
(c) a network stabilizer;
(d) a thixotropic agent; and
(e) a pigment.

2. The blood partitioning composition of claim 1, wherein
(a) said poly-alpha-pinene is present within the range of between about 67 and 86 percent by weight; and
(b) said chlorinated hydrocarbon is present within the range of between about 13 and 24 percent by weight.

3. The composition of claim 1, wherein
(a) said chlorinated hydrocarbon has a chlorine content of at least 50 percent by weight.

4. A blood partitioning composition characterized by an admixture forming a thixotropic gel, said gel composition comprising
(a) a resin blend of poly-alpha-pinene and chlorinated octadecene;
(b) epoxidized soybean oil;
(c) short chain polyfunctional network stabilizer;
(d) silica; and
(e) titanium dioxide.

5. The composition of claim 5 wherein
(a) said composition has a specific gravity of within the range of between about 1.03 and 1.07 at 25° C.

6. The composition of claim 5, wherein
(a) said composition has a viscosity of within the range of between 800,000 and 1,800,000 centipoises at 35° C.

7. A blood partitioning composition characterized by an admixture forming a thixotropic gel, said gel comprising
(a) a dual resin component including within the range of between about 67 and 86 percent by weight of poly-alpha-pinene combined with within the range of between about 13 and 24 percent by weight of chlorinated octadecene;
(b) within the range of between about 2 and 6 percent by weight of a thixotropic agent;
(c) within the range of between about 0.015 and 0.03 percent by weight of a pigment;
(d) within the range of between about 0.15 and 0.8 percent by weight of a network stabilizer; and
(e) within the range of between about 2.3 and 15 percent by weight of a radiation stabilizer.

8. A blood collection assembly characterized by
(a) an evacuated tube;
(b) said evacuated tube having a closed end and an open end;
(c) an elastomer stopper for closing said open end and maintaining the vacuum in said evacuated tube; and
(d) a blood partitioning composition in said evacuated tube, said composition comprising
(1) a dual resin component including poly-alpha-pinene of lower density combined with a chlorinated octadecene of higher density;
(2) a radiation stabilizer;
(3) a network stabilizer;
(4) a thixotropic agent; and
(5) a pigment.

* * * * *